(12) United States Patent
Hakkens et al.

(10) Patent No.: US 11,471,128 B2
(45) Date of Patent: Oct. 18, 2022

(54) ULTRASONIC HEAD COMPRISING A PLIABLE COVER WITH A REGULAR PATTERN OF APERTURES

(71) Applicant: KONINKLIJKE PHILIPS N.V., Eindhoven (NL)

(72) Inventors: Franciscus Johannes Gerardus Hakkens, Eersel (NL); David Andrew Fish, Worthing (GB); Lucas Johannes Anna Maria Beckers, Veldhoven (NL); Antonius Maria Rijken, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 890 days.

(21) Appl. No.: 16/310,424

(22) PCT Filed: Jun. 12, 2017

(86) PCT No.: PCT/EP2017/064237
§ 371 (c)(1),
(2) Date: Dec. 15, 2018

(87) PCT Pub. No.: WO2017/216084
PCT Pub. Date: Dec. 21, 2017

(65) Prior Publication Data
US 2019/0328359 A1    Oct. 31, 2019

(30) Foreign Application Priority Data
Jun. 17, 2016  (EP) ..................... 16174922

(51) Int. Cl.
*A61B 8/00*     (2006.01)
*A61N 7/00*    (2006.01)
(Continued)

(52) U.S. Cl.
CPC .......... *A61B 8/4281* (2013.01); *A61B 8/4455* (2013.01); *A61B 8/4209* (2013.01);
(Continued)

(58) Field of Classification Search
CPC ... A61B 8/4281; A61B 8/4455; A61B 8/4209; A61B 8/4477; A61B 8/4272;
(Continued)

(56) References Cited

U.S. PATENT DOCUMENTS 5,394,877 A * 3/1995 Orr ........................ A61B 5/25
600/459
5,400,785 A    3/1995 Crowley
(Continued)

FOREIGN PATENT DOCUMENTS

KR     20030014548 A    2/2003
RU       2383372 C2     3/2010

OTHER PUBLICATIONS

International Search Report and Written Opinion for International Application No. PCT/EP2017/064237, dated Sep. 25, 2017, 14 pages.

*Primary Examiner* — Sean D Mattson (57) ABSTRACT

A pliable cover adapted to cover an active area of an ultrasound probe is described. The ultrasound probe includes a plurality of ultrasound transducer elements. The pliable cover includes a polymer layer that holds a coupling agent (4) that couples the ultrasound transducer elements to a body surface and a regular pattern of channels extending through the pliable cover. An ultrasound probe arrangement
(Continued)

is also described and includes the pliable cover. An ultrasound system including the ultrasound probe arrangement, and a method of positioning the ultrasound probe in a region of a body are also described.

21 Claims, 8 Drawing Sheets

(51) Int. Cl.
    *G01S 15/89* (2006.01)
    *H01L 41/053* (2006.01)
    *A61N 7/02* (2006.01)

(52) U.S. Cl.
    CPC ........ *A61N 7/02* (2013.01); *A61N 2007/0078* (2013.01); *G01S 15/8915* (2013.01); *H01L 41/053* (2013.01)

(58) Field of Classification Search
    CPC .......... A61B 8/4444; A61N 7/02; A61N 7/00; A61N 2007/0078; A61N 2007/0052; H01L 41/053; G01S 15/8915
    See application file for complete search history.

(56) References Cited

U.S. PATENT DOCUMENTS

| | | | |
|---|---|---|---|
| 6,039,694 A * | 3/2000 | Larson | A61B 8/4281 600/459 |
| 6,500,141 B1 | 12/2002 | Irion et al. | |
| 2005/0215901 A1 * | 9/2005 | Anderson | A61B 8/12 600/445 |
| 2006/0235303 A1 | 10/2006 | Vaezy et al. | |
| 2007/0208280 A1 | 9/2007 | Talish et al. | |
| 2009/0036773 A1 | 2/2009 | Lau et al. | |
| 2010/0204577 A1 | 8/2010 | Sekins et al. | |
| 2011/0270137 A1 | 11/2011 | Goren et al. | |
| 2012/0277640 A1 | 11/2012 | Lewis, Jr. et al. | |
| 2013/0165005 A1 * | 6/2013 | Berard-Andersen | A61B 8/4236 442/65 |
| 2014/0163375 A1 * | 6/2014 | Wasielewski | A61B 8/4427 600/443 |
| 2017/0128042 A1 * | 5/2017 | Desai | A61B 8/4422 |
| 2017/0311923 A1 * | 11/2017 | Saberi | A61B 8/4427 |

* cited by examiner

ULTRASONIC HEAD COMPRISING A PLIABLE COVER WITH A REGULAR PATTERN OF APERTURES

This application is the U.S. National Phase application under 35 U.S.C. § 371 of International Application No. PCT/EP2017/064237, filed on Jun. 12, 2017, which claims the benefit of European Application Serial No. 16174922.1, filed Jun. 17, 2016. These applications are hereby incorporated by reference herein.

FIELD OF THE INVENTION

The present invention relates to a pliable cover for covering an active area of an ultrasound probe comprising a plurality of ultrasound transducer elements.

The present invention further relates to an ultrasound probe assembly comprising an ultrasound probe covered by such a pliable cover.

The present invention further relates to an ultrasound system comprising such an ultrasound probe assembly.

The present invention further relates to a method of applying an ultrasound probe to a body region.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by an ultrasound device comprising ultrasound transducer element tiles and are focused on diseased tissue. The significant energy deposition at the focus creates local temperatures in the range of about 65° C. to 85° C., which destroys the deceased tissue by coagulative necrosis.

Such ultrasound systems typically comprise an ultrasound probe for delivering ultrasound waves to a subject, e.g. to a patient being imaged or treated. Such an ultrasound probe typically comprises a plurality of ultrasound transducers such as piezoelectric transducer elements formed of materials such as lead zirconate titanate (PZT) or polyvinylidenefluoride (PVDF) and capacitive micro-machined ultrasonic transducer (CMUT) elements in which a membrane including a first electrode over a cavity comprising a second electrode opposite the first electrode and separated therefrom by the cavity is used to generate the ultrasound waves (or receive the ultrasound waves in a receive mode) through application of an appropriate stimulus, e.g. an alternating current, to the first and second electrodes. Increasingly, several of such ultrasound transducer elements are combined on so-called tiles, e.g. chips of a semiconductor substrate in which the ultrasound transducer elements, which tiles may have dimensions of several centimetres squared in some applications. This allows for the ultrasound probes to cover larger areas of the subject's body to be imaged or treated. The ultrasound transducer elements of such tiles may be grouped together and operated in unison, such that the tile behaves as a composite ultrasound transducer element comprising multiple facets, i.e. ultrasound transducer cells combining to form the composite ultrasound transducer element, or alternatively may be operated independently.

For such ultrasound probes, and in particular for large area ultrasound probes, e.g. ultrasound probes comprising a plurality of such ultrasound transducer tiles, it is far from trivial to establish a good conformal contact between the transducer elements of the ultrasound probe and the part of the body to be imaged. For smaller ultrasound probes, this is typically achieved by using special gels that improve the contact between the ultrasound transducer array and the body part. However, a drawback of this approach is that usually large amounts of gel have to be used, which may contain air bubbles that interfere with the transmission or reception of the ultrasound signals.

Also, such gel applications may no longer be practically feasible for large area ultrasound probes, as it becomes practically impossible to effectively apply the gel to the individual transducer elements, e.g. tiles without this process becoming messy due to the use of excess gel. This is particularly problematic for large-area ultrasound probes that are designed such that upon contact with the subject's body, the ultrasound transducer elements are sealed against the subject's body, e.g. by the creation of a sealed space between the ultrasound transducer elements and the subject's body in which an underpressure is created relative to ambient pressure, e.g. by evacuating some of the air from between the ultrasound probe and the subject's body with a vacuum pump or the like. The presence of large amounts of gel may block the tubing to the vacuum pump upon evacuation of the air from the sealed space, which is undesirable, e.g. from a maintenance perspective.

US 2011/0264012 A1 discloses an elastomeric pad structure coupled to an ultrasonic transducer. The material and shape of the face of the pad structure traps a small amount of liquid between the pad and the skin, providing an effective coupling agent not requiring further containment, rewetting, or clean-up. However, such a pad does not allow evacuation of a volume of air from a sealed space in the aforementioned ultrasound probes to seal the probe against a patient's body.

SUMMARY OF THE INVENTION

The present invention seeks to provide pliable cover for covering an active area of an ultrasound probe comprising a plurality of ultrasound transducer elements that allows for evacuation of air from a sealed space between the ultrasound probe and the body.

The present invention further seeks to provide an ultrasound probe assembly comprising an ultrasound probe covered by such a pliable cover.

The present invention further seeks to provide an ultrasound system comprising such an ultrasound probe assembly.

The present invention further seeks to provide a method of applying an ultrasound probe to a body region using such a pliable cover.

According to an aspect, there is provided a pliable cover for covering an active area of an ultrasound probe comprising a plurality of ultrasound transducer elements, the cover comprising a polymer layer for containing a coupling agent for coupling the ultrasound transducer elements to a body surface and a regular pattern of channels extending through the pliable cover. The channels act as evacuation holes through which air between the pliable cover and the patient's body may be evacuated upon connecting the sealed space between the ultrasound probe and the patient's body to an air extraction device such as a fan or vacuum pump, thereby achieving a good conformal contact between the pliable cover and the patient's body, whereby the coupling agent ensures a good conformal contact between the ultrasound transducer elements and the pliable cover.

Preferably, the channels are positioned such that when the pliable cover is covering the active area, the channels are arranged in between the ultrasound transducer elements. This ensures that the entirety of the area of the ultrasound transducer elements is contacted by the pliable cover, which ensures optimal acoustic behaviour of the ultrasound transducer elements.

The coupling agent may be separately applied to the pliable cover, e.g. in case of a non-disposable pliable cover or may form a part of the pliable cover, e.g. in case of a disposable pliable cover. For example, the polymer layer may be coated with the coupling agent, the coupling agent may be dissolved or absorbed in the polymer layer or the coupling agent may be contained by opposing polymers layers, wherein at least the polymer layer arranged to face the active area is porous or permeable to the coupling agent.

The coupling agent preferably is a liquid, an oil, an oil-based emulsion, a wax or a gel. The coupling agent is typically selected to achieve good wetting of the respective surfaces of the ultrasound transducer elements brought into contact with the coupling agent.

In order to facilitate affixing of the pliable cover to the ultrasound probe, the pliable cover may further comprise a frame affixed to an edge of the cover for mounting the cover onto the ultrasound probe. Such a frame may be a flexible frame, e.g. made of an elastomer material, to promote sealing of the frame against the ultrasound probe and the patient's body. Alternatively, the pliable cover may comprise an adhesive edge region for adhering the cover to the ultrasound probe.

In an embodiment, the pliable cover has a thickness in a range of 10-1,000 μm. When the pliable cover has a thickness in this range, a good conformal contact between the ultrasound probe and the patient's body may be achieved without significantly affecting the acoustic performance of the ultrasound probe.

According to another aspect, there is provided an ultrasound probe assembly comprising an ultrasound probe including a probe body having a mounting area and a flexible lip around said mounting area for sealing a space between the mounting area and a subject contacted by the ultrasound probe; and an active area comprising a plurality of ultrasound transducer elements mounted in the mounting area; and the pliable cover according to any embodiments of the present invention covering the active area. Such an ultrasound probe assembly may achieve good quality conformal contact between the ultrasound probe and the patient's body without requiring large amounts of a coupling gel. The ultrasound probe assembly may further comprise affixing means affixing the pliable cover to the ultrasound probe.

In an embodiment, the mounting area is a pliable mounting area having a corrugated shape, the ultrasound probe further comprising a support member having pillars engaging with the pliable mounting area, each of said pillars being attached to a mounting portion for mounting an individual transducer element. Such a mounting area can be collapsed towards the patient's body by evacuation of a volume of air from the sealed space between the ultrasound probe and the patient's body, which aids the establishment of a good-quality conformal contact between the ultrasound transducer elements and the patient's body.

According to yet another aspect, there is provided an ultrasound system comprising the ultrasound probe assembly of any of the embodiments of the present invention. Such an ultrasound system benefits from the good-quality conformal contact between the ultrasound transducer elements and the patient's body, which for instance aids the generation of high-quality ultrasound images in case of an ultrasound imaging system or effective delivery of ultrasound waves to a target region in the patient's body in case of an ultrasound therapy system.

According to still another aspect, there is provided a method of applying an ultrasound probe to a body region, the method comprising providing an ultrasound probe including a probe body having a mounting area and a flexible lip around said mounting area for sealing a space between the mounting area and a subject contacted by the ultrasound probe; and an active area comprising a plurality of ultrasound transducer elements mounted in the mounting area; affixing the pliable cover according to any of the embodiments of the present invention over the active area to form an ultrasound probe assembly; positioning the ultrasound probe assembly on the body region; and evacuating a volume of air from the space to create an underpressure in said space causing the pliable cover to conform to the respective surfaces of the transducer elements. Such a method enables the establishment of a good-quality conformal contact between the ultrasound transducer elements and the patient's body without requiring large amounts of coupling gel. However, a reduced amount of coupling gel may still be applied to the body region prior to positioning the ultrasound probe assembly thereon to further aid the establishment of such a good-quality conformal contact.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
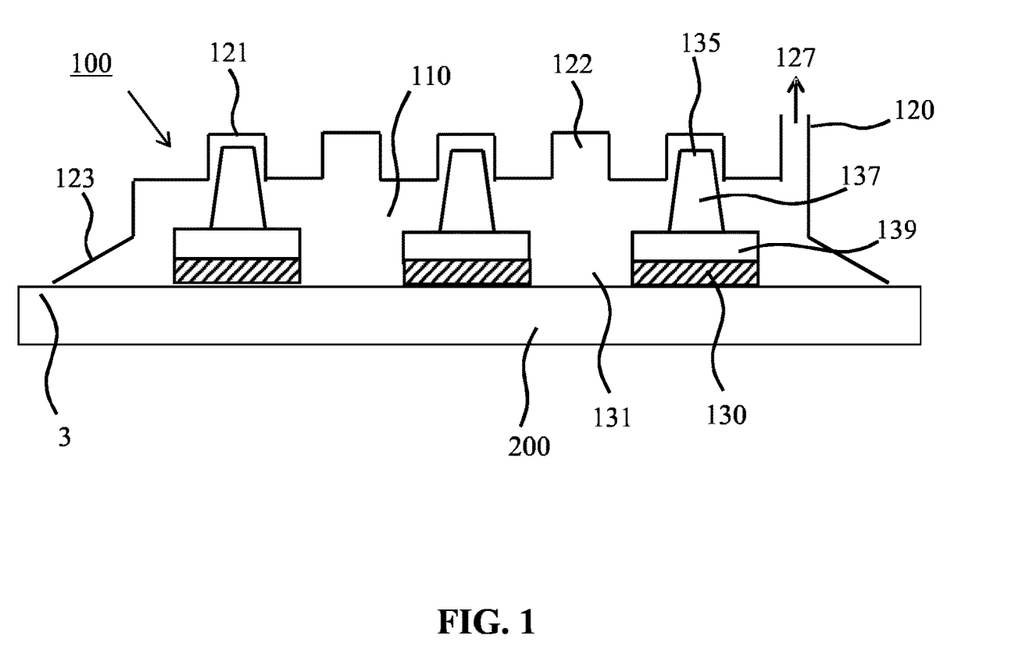
FIG. 1 schematically depicts an example embodiment of an ultrasound transducer probe.

FIG. 1 shows an example embodiment of an ultrasound probe 100 having a transducer array comprising ultrasound transducer element tiles 130 comprising one or more ultrasound transducer elements (not shown). Each tile 130 for example may be a diced chip or the like onto which the one or more ultrasound transducer elements have been formed or mounted. In the present invention, the ultrasound transducer elements may be implemented in any suitable manner. For example, the ultrasound transducer elements may be implemented by a piezoelectric ceramic material such as a lead zirconate titanate (PZT)-based material, a piezoelectric single crystal or composite material, a capacitive micromachined ultrasound transducer (CMUT) and so on.

The ultrasound transducer element tiles 130 may have any suitable shape, e.g. a circular shape or polygonal shape. A polygonal shape such as a rectangular, e.g. square, shape is particularly mentioned as such a shape facilitates a close packing of the ultrasound transducer element tiles 130 within the transducer array, wherein the gap 131 between adjacent ultrasound transducer element tiles 130 is minimized. The avoidance of relatively large gaps 131 between adjacent ultrasound transducer element tiles 130 ensures that a substantially continuous image may be generated with the ultrasound probe 100 and may at least reduce the formation of ultrasound artifacts such as grating lobes.

The transducer array may have any suitable shape, e.g. may be a 1-dimensional or 2-dimensional transducer array. Alternatively, the transducer array may be composed of individual ultrasound transducer elements. In a preferred embodiment, the ultrasound probe 100 comprises a plurality of ultrasound transducer tiles 130, each having a transducer surface area of several cm2, e.g. 2-50 cm2, to form a large area ultrasound probe 100.

The ultrasound probe 100 may be for transmitting ultrasonic waves, e.g. ultrasound pulses, and receiving (pulse) echo information in case the ultrasound probe 100 forms part of an ultrasound diagnostic imaging system. Alternatively, the ultrasound probe 100 may be adapted to generate focused ultrasound waves in case the ultrasound probe 100 forms part of an ultrasound therapy system such as a HIFU therapy system.

Figure 2:
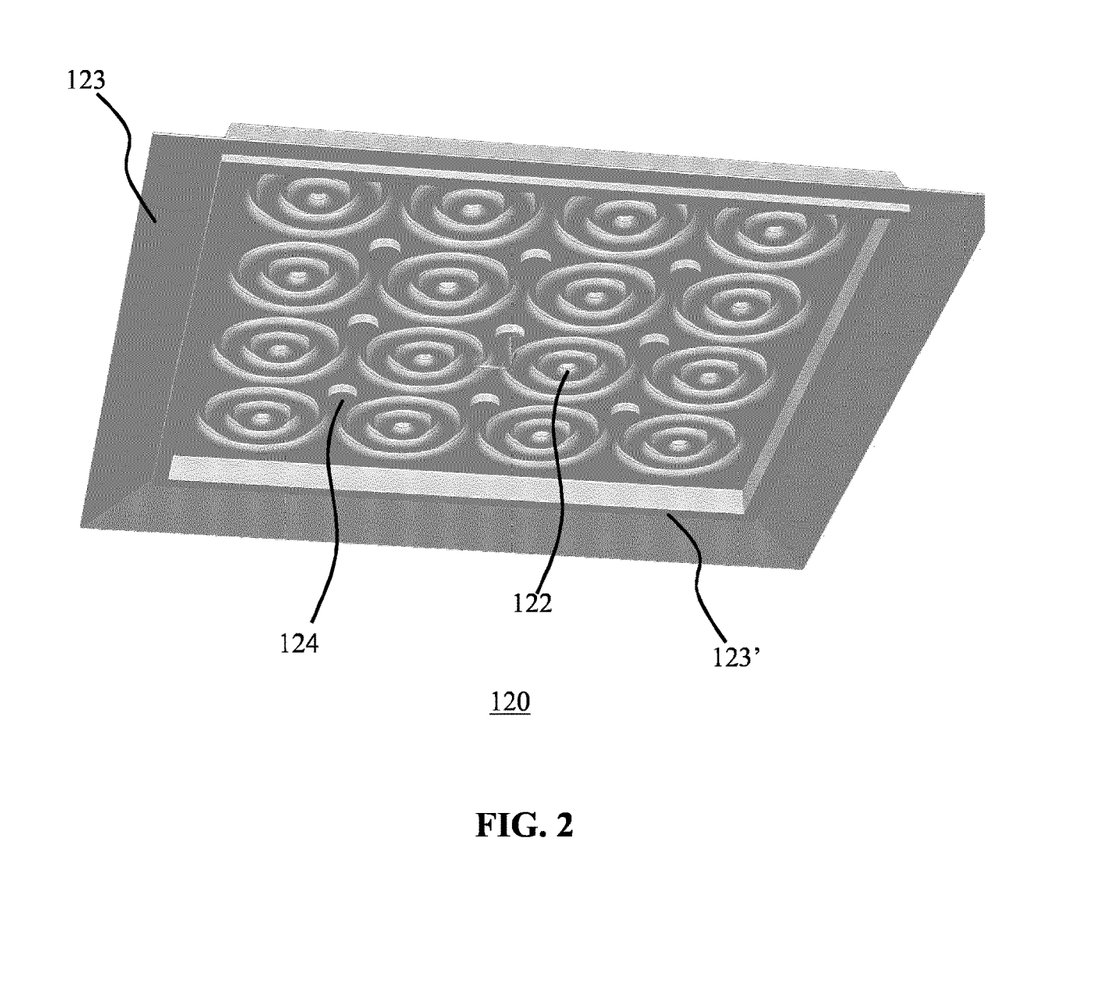
FIG. 2 schematically depicts a perspective view of a further aspect of the ultrasound probe according to FIG. 1.

The ultrasound probe 100 typically comprises a probe body 120 having a mounting region 121 onto which the ultrasound transducer element tiles 130 are mounted. A detail of such a probe body 120 is schematically depicted in FIG. 2. Although not shown, the transducer surfaces of the ultrasound transducer element tiles 130 may be covered by an acoustic layer, sometimes referred to as an acoustic window, in order to protect the ultrasound transducer array from being directly contactable, thereby protecting the transducer array from damage, as well as to protect the body of the subject 200, e.g. a patient, to be exposed to the ultrasound waves to be generated by the transducer array from being directly contacted by the transducer array, e.g. to protect the body from accidental electrical shock. As is well-known per se, such an acoustic window may further provide impedance matching between the transducer array and the body. The acoustic layer may be made of any material or combinations of materials known to the skilled person for such purposes.

The mounting region 121 of the probe body 120 may be rigid, e.g. may be a rigid carrier of the ultrasound transducer element tiles 130. Any suitable rigid material may be used for this purpose. Alternatively, the mounting region 121 may be flexible, which has the advantage that the mounting region 121 carrying the ultrasound transducer element tiles 130 may be deformed, e.g. to conform to a non-planar surface such as a contoured body of a patient to improve the quality of contact between the ultrasound transducer element tiles 130 and the patient's body. This is particularly relevant in case of large area ultrasound probes 100, where the probe may need to conform to a large area of the patient's body, e.g. an area of several tens or hundreds of cm2. For example, the mounting region 121 may comprise an elastomer, i.e. a rubbery material, to provide the mounting region 121 with the desired flexibility. Examples of such an elastomer include a polyolefin, a diene polymer or a polysiloxane such as PDMS, a co-polymer or block-copolymer comprising a polyolefin, a diene polymer or a polysiloxane or a blend thereof although embodiments are not limited thereto. Polybutadiene, polydimethylsiloxane (PDMS) and relatively soft polyether block amides (PEBA) commonly used in catheters, are specifically mentioned. A medical grade PDMS is particularly preferred. For example, the ultrasound probe 100 may be implemented as a flexible mat for conforming to the surface (body) of the subject 200.

Figure 3:
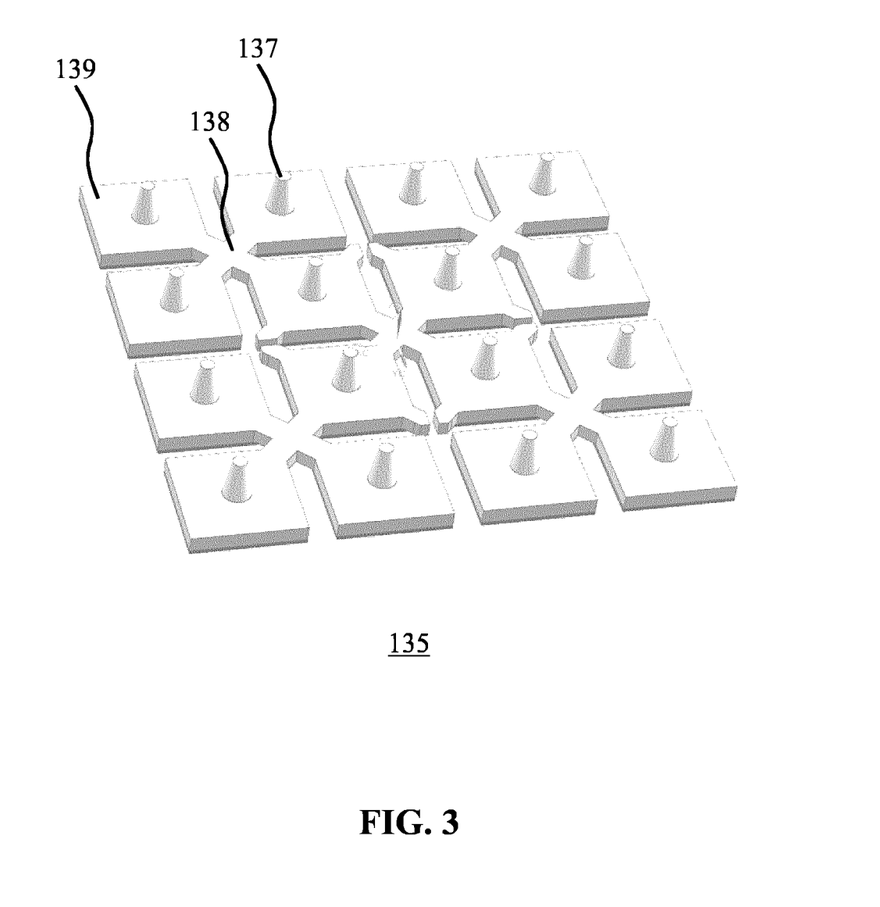
FIG. 3 schematically depicts a perspective view of a yet a further aspect of the ultrasound probe according to FIG. 1.

The ultrasound transducer element tiles 130 may be directly mounted onto the mounting region 121 in some embodiments (not shown). In alternative embodiments, such as the embodiment schematically depicted in FIG. 1, the mounting region 121 may comprise a plurality of receiving portions 122 for receiving a support member onto which an ultrasound transducer element tile 130 may be mounted. A detail of such a support member is schematically depicted in FIG. 3. The support members may each comprise a pillar 137 that fits into one of the receiving portions 122 of the mounting region 121. Each pillar 137 carries a mounting portion 139 onto which the ultrasound transducer element tile 130 may be mounted. The support members may be made of a flexible material, e.g. a rubber-like material, and may be interconnected through mounting portions 139, e.g. to form a flexible mat 135 through interconnecting regions 138 in between adjacent mounting portions 139.

As shown in FIG. 3, each interconnecting region 138 groups four quadrants of mounting portions 139 that each have a corner interconnected to the interconnecting region 138. In this manner, each tile 130 will exhibit at least two degrees of rotational freedom, such that a good conformal contact with the body of the subject 200 can be achieved when the pressure in the space 110 is reduced by evacuation of a portion of air as explained in more detail below, with the resulting downward force on the mounting portions 139 as transferred through the pillars 137 being translated into the desired conformal contact of the tiles 130 through these rotational degrees of freedom. In an alternative embodiment, the support member arrangement, e.g. mat 135 may be a rigid arrangement in which the mounting regions 139 are mounted on a flexible joint, e.g. a universal joint, a ball and socket joint, or the like.

The mounting region 121 is typically delimited by a flexible lip 123 that is arranged to contact the subject 200 upon placement of the ultrasound probe 100 on the subject 1. The lip 123 is flexible such that upon placement of the ultrasound probe 100 on the subject 200, the lip 123 seals a space 110 in between the mounting region 121 of the probe body 120 and the part of the subject's body opposite the mounting region 121. The lip 123 may form an integral part of the probe body 120, or may be adhered or otherwise attached to the mounting region 121. In the context of the present application, the lip 123 may have any suitable shape that facilitates the formation of a sealed space 110 in between the ultrasound transducer element tiles 130 and the body of the subject 1 upon placement of the ultrasound probe 100 on this body. The flexible lip 123 may be made of any suitable material, e.g. an elastomer as described above. In an embodiment, the mounting region 121 and the flexible lip 123 are made of the same material, with the flexible lip 123 preferably being integral to the mounting region 121, i.e. being formed from a single piece of flexible material. In an embodiment as depicted in FIG. 2, the lip 123 may include an edge 123' or may be separated from the space 110 by the edge 123', which edge 123' engages with the subject 1 to reinforce the mounting region 121 in case of the pressure in the space 110 being reduced. The edge 123' may further assist in forming a seal between the ultrasound probe 100 and the subject 1 such that an underpressure can be established in the space 110 as explained above.

The mounting region 121 of the probe body 120 may further comprise support portions 124 in between the receiving portions 122 that reinforce the mounting region 121 in case of the pressure in the space 110 being reduced. The mounting region 121 may be corrugated as schematically depicted in FIG. 1 such that the mounting region can act as a spring. Consequently, when a volume of air is evacuated from the space 110 through outlet 127, e.g. using a vacuum pump or the like, to create an underpressure in the space 110, the atmospheric pressure over the probe 100 forces the sprung mounting region 121 against the body. As little as a 10% reduction in pressure in the space 110 may suffice to achieve a downward pressure of 1 N/cm$^2$ on the mounting region 121.

As will be readily understood by the skilled person, in order to achieve the desired acoustic coupling (also referred to as conformal coupling) between the respective ultrasound transducer elements 130 and the body of the subject 200, a coupling gel such as a glycerin gel traditionally was applied to the ultrasound probe 100. However, for an ultrasound probe arranged to be sucked against the patient's body, such as the ultrasound probe 100 as schematically depicted in FIG. 1, the application of such a coupling gel is rather cumbersome, as the gel needs to be applied to each individual transducer element, e.g. tile, 130. It is difficult to avoid the gel spilling into the gaps 131 between the respective transducer elements 130, which may cause the gel to be sucked into the outlet 127 and the tubing attached to this outlet when trying to establish the underpressure in the sealed space 110.

Embodiments of the present invention seek to provide a pliable coupling foil, i.e. cover, that may be applied over the active area of the ultrasound probe 100, which pliable cover at least reduces the amount of a coupling agent required to establish the desired acoustic coupling between the respective transducer elements 130 and the patient's body. Such a foil or cover may have a thickness ranging from 10-1,000 μm to ensure sufficient pliability of the foil or cover whilst at the same time facilitating a good acoustic coupling of the ultrasound transducer elements 130 to the patient's body.

Figure 4:
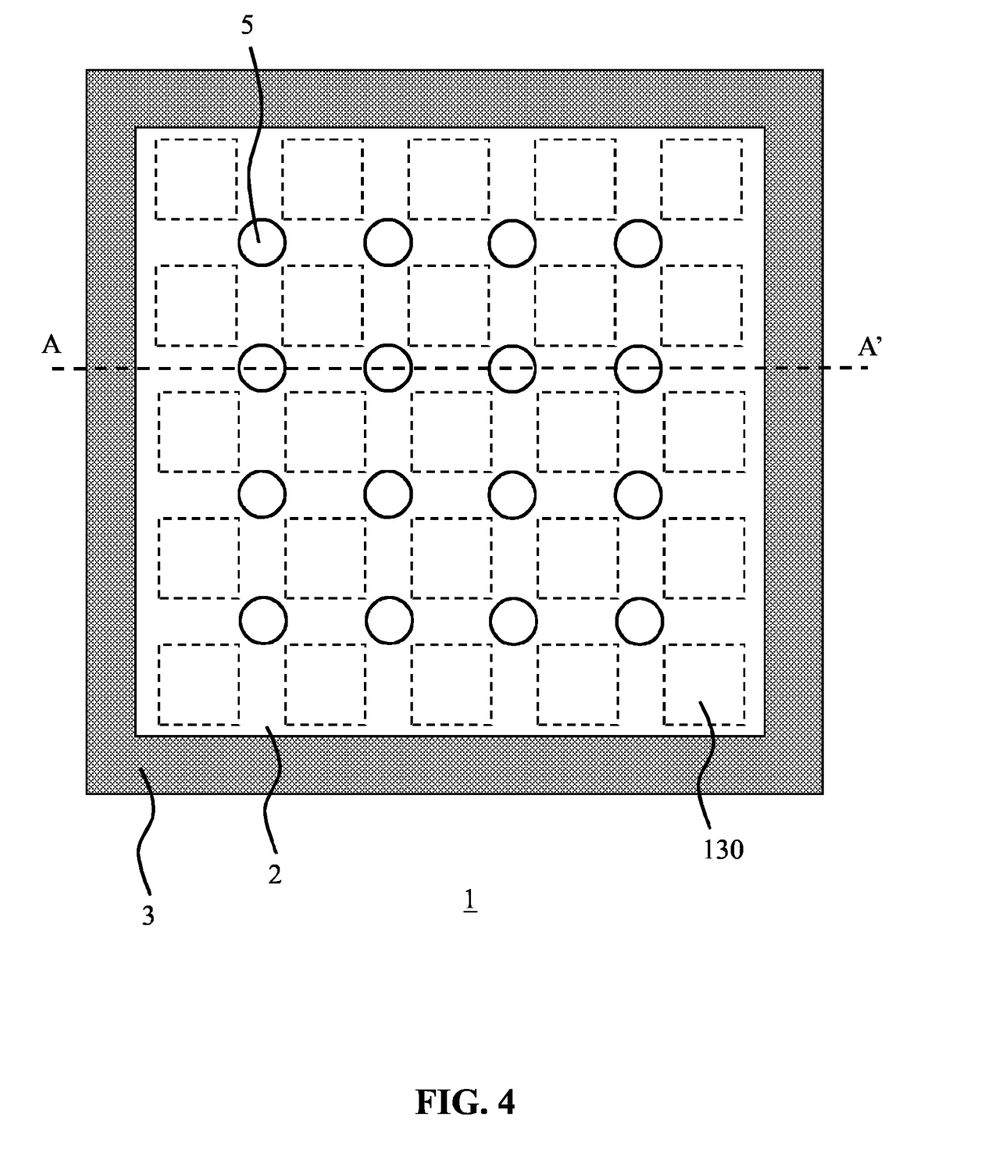
FIG. 4 schematically depicts a top view of a pliable cover according to an embodiment.

FIG. 4 schematically depicts a top view of such a pliable cover or foil 1, comprising a polymer layer or film 2 suspended in a frame 3. The pliable cover 1 further comprises regular pattern of channels 5 extending through the polymer layer 2 such that upon positioning of the pliable cover 1 over the active area of the ultrasound transducer array 100, the channels 5 align with the gaps 131 in between the ultrasound transducer elements 130. In this manner, air can be evacuated from in between the pliable cover 1 and a region of the body of the subject 200 onto which the pliable cover 1 is placed.

The polymer layer 2 may be an elastomer layer to provide the pliable cover 1 with the desired pliability. Such an elastomer preferably is a biocompatible elastomer, e.g. a styrene-ethylene/butylene styrene (SEBS) elastomer, a polybutadiene rubber, a polyurethane, a polymethylpentene such as TPX® as marketed by Mitsui Chemicals America Inc., a polysiloxane elastomer such as polydimethylsiloxane (PDMS) or a silicone by way of non-limiting example. Other suitable polymers will be immediately apparent to the skilled person. Alternatively or additionally, the polymer layer 2 may comprise a hydrogel material.

In some embodiments, the polymer layer 2 may further comprise a particulate material distributed through the polymer layer, e.g. metal particles, metal oxide particles, ceramic particles, or the like, for impedance matching the polymer layer 2 to the acoustic impedance of the ultrasound transducer elements 130 or the permanent acoustic window (matching layer) or lens applied to the transducing surface of the ultrasound transducer elements 130. Examples of such acoustic window or lens materials include silicone, Pebax, TPX, to name but a few examples. Many other examples will be immediately apparent to the skilled person. In some embodiments, the thickness of the acoustic window or lens may be reduced such that the desired acoustic impedance matching is achieved by the combination of the acoustic window or lens and the polymer layer 2.

The frame 3 may be a rigid frame or a flexible frame for mounting the pliable cover 1 to the ultrasound probe 100 using suitable affixing means, e.g. clamps, clips, screws, an adhesive strip covering part of the frame 3 and so on. Alternatively, in case of a flexible frame 3, the frame may be stretched such that the frame is lifted over an outer edge or rim of the ultrasound probe 100, such that upon relaxing the frame 3, the frame is secured against this outer edge or rim. The frame 3 may be made of a rigid polymer, a flexible polymer such as a rubber or elastomer, a metal, a metal alloy, and so on, or any combination of such materials. The frame 3 may act as a seal between the ultrasound probe 100 and the body of the subject 200, in which case the lip 123 may be omitted from the ultrasound probe 100. To this end, the frame 3 for example may comprise an elastomer seal arranged to face the body of the subject 200 during normal use of the pliable cover 1. Alternatively or additionally, the frame 3 may comprise an elastomer seal arranged to engage with the ultrasound probe 100 during normal use of the pliable cover 1, e.g. to seal the space 110.

The polymer layer 2 may be affixed to the frame 3 in any suitable manner. For example, the polymer layer 2 may be affixed to the frame 3 by thermocompression, gluing, ultrasonic bonding and/or by some mechanical fixation, e.g. using clamps, screws, nails, staples, or the like. Alternatively, the frame 3 may be omitted from the pliable cover 1, in which case the pliable cover 1 for instance may comprise an adhesive edge region that during normal use is brought into contact with the ultrasound probe 100 for adhering the pliable cover 1 to the ultrasound probe, or alternatively may comprise a plurality of perimeter holes for engaging with fastening members, e.g. hooks or the like, along a perimeter of the ultrasound probe 100. Other fastening techniques for securing the pliable cover 1 to the ultrasound probe 100 equally may be contemplated.

In some embodiments, the pliable cover 1 may be a disposable cover or foil that further comprises a coupling agent such as a liquid, e.g. water, a polar or non-polar organic solvent, etcetera, an oil, e.g. a silicone oil, a plant-based oil, a mineral oil, etcetera, an oil-based emulsion, a wax or a gel, e.g. a hydrogel, paraffin, glycerine, or the like.

Figure 5:
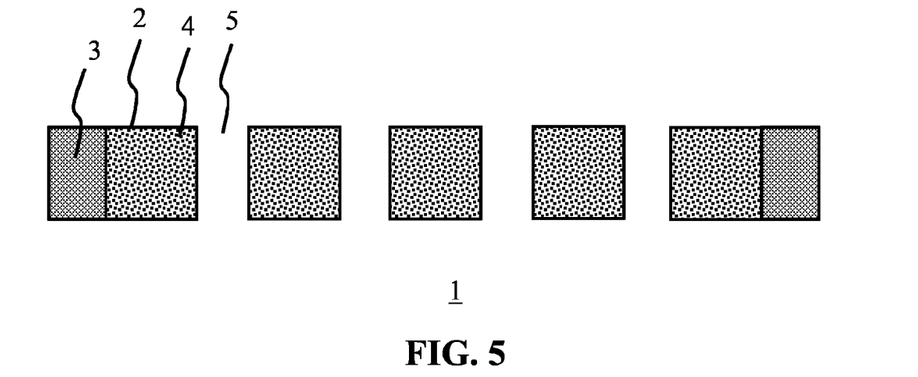
FIG. 5 schematically depicts a cross-section of a pliable cover according to an embodiment.

FIG. 5 schematically depicts a cross-section section of an embodiment of such a disposable pliable cover 1 along the dotted line A-A' in FIG. 4 in which the coupling agent 4 is contained within the polymer layer 2, e.g. by impregnating or otherwise providing a polymer layer 2 with the coupling agent 4, by dissolving the coupling agent 4 in the polymer layer 2, and so on. Such polymers are well-known per se; for example, the polymer layer 2 may be a SEBS polymer containing a mineral oil or paraffin, a polybutadiene rubber filled with oil, a silicone polymer filled with silicone oil, a hydrogel filled with water, and so on.

Figure 6:
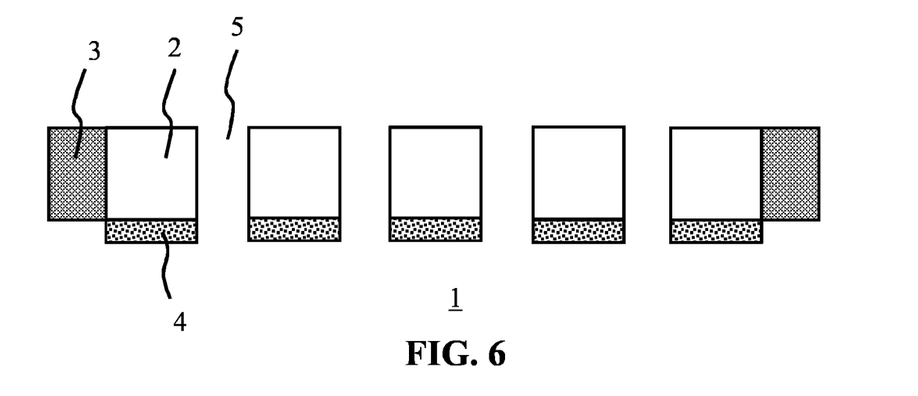
FIG. 6 schematically depicts a cross-section of a pliable cover according to another embodiment.

FIG. 6 schematically depicts a cross-section section of another embodiment of such a disposable pliable cover 1 along the dotted line A-A' in FIG. 4 in which the coupling agent 4 is coated onto the polymer layer 2. Although in FIG. 6 only a single surface of the polymer layer 2 is coated with the coupling agent 4, it should be understood that it is equally feasible that both opposing major surfaces of the polymer layer 2 are coated with the coupling agent 4.

Figure 7:
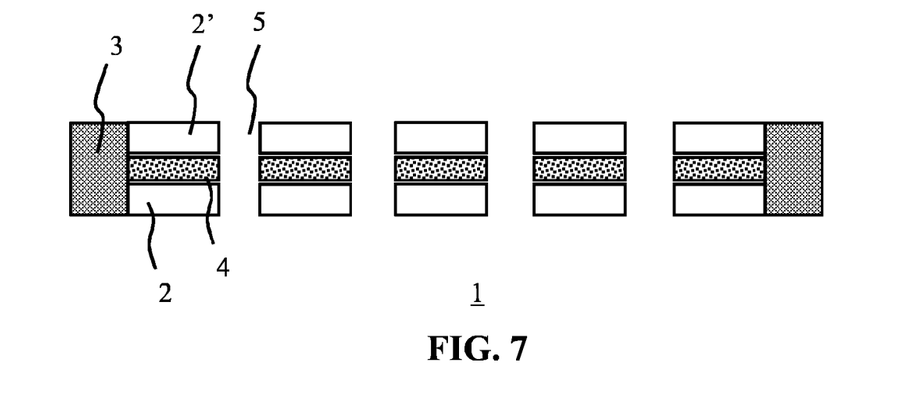
FIG. 7 schematically depicts a cross-section of a pliable cover according to yet another embodiment.

FIG. 7 schematically depicts a cross-section section of another embodiment of such a disposable pliable cover 1 along the dotted line A-A' in FIG. 4 in which the coupling agent 4 is contained (sandwiched) between the polymer layer 2 and an opposing polymer layer 2'. In this embodiment, at least one of the polymer layers 2, 2' is a porous or otherwise permeable layer to facilitate the migration of the coupling agent 4 to at least one of the major surfaces of the pliable cover 1, typically the major surface for contacting the ultrasound transducer elements 130 although both polymer layers may be porous or otherwise permeable such that the coupling agent 4 may migrate to both major surfaces of the pliable cover 1, e.g. when exposed to an underpressure as created via the outlet 127 of the ultrasound probe 100 as explained above.

The coupling agent 4 may be selected to be compatible with the polymer layer 2, 2' and/or the transducer elements 130. In an embodiment, the coupling agent 4 is selected to have good wettability on the permanent acoustic windows of the ultrasound transducer elements 130 (or on the major surfaces of the ultrasound transducer elements 130 in the absence of such a permanent acoustic window). For example, where the individual transducer elements 130 comprise a silicone acoustic window, the coupling agent 4 may be a silicone oil, e.g. a silicone polymer impregnated or otherwise provided with a silicone oil. If the outer surface of such an acoustic window is a polymethylpentene such as TPX, the coupling agent 4 may be a non-polar fluid, e.g. a non-polar solvent, oil, emulsion, wax, gel or the like. It will be immediately apparent to the skilled person that these are non-limiting examples only and that there are many other suitable combinations of acoustic window materials and coupling agents 4 that may be contemplated.

In the above embodiments, the pliable cover 1 typically is a disposable cover containing the coupling agent 4. However, in alternative embodiments, the pliable cover 1 may be reusable, e.g. washable and/or sterilizable for reuse. In such embodiments, the pliable cover 1 may be supplied including the coupling agent 4, with the user needing to reapply the coupling agent 4 after washing and sterilizing the pliable cover 1, or alternatively may supplied excluding the coupling agent 4, such that the user must apply the coupling agent 4 to the pliable cover 1 prior to first use as well.

Figure 8:
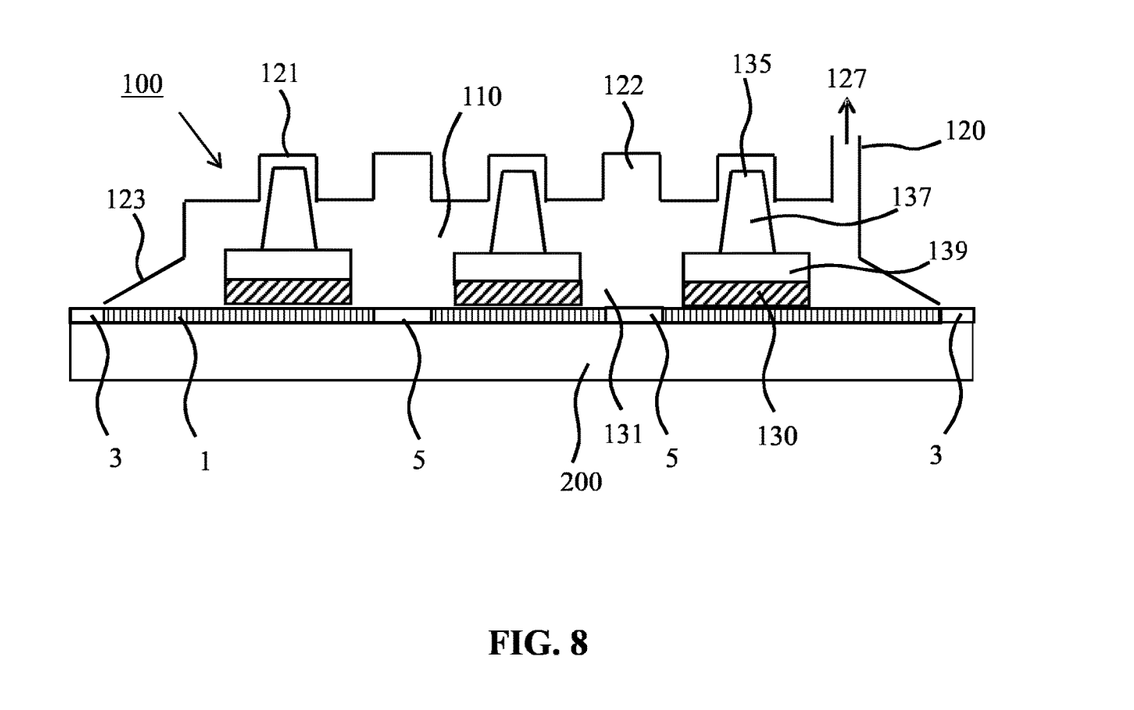
FIG. 8 schematically depicts an ultrasound transducer probe assembly according to an embodiment.

FIG. 8 schematically depicts a cross-section of an ultrasound transducer probe assembly including an ultrasound transducer probe 100 and a pliable cover 1 affixed to the ultrasound probe 100 according to an embodiment. As can be seen in FIG. 8, the channels 5 are aligned with the gaps 131 in between the ultrasound transducer elements 130 such that air can be sucked from in between the pliable cover 1 and the body of the patient on one side and that ultrasound transducer elements 130 on the other side of the pliable cover 1, e.g. by evacuating a volume of air from the space 110 to outlet 127 using an air evacuation device such as a fan or a vacuum pump, or by pressing the ultrasound transducer probe assembly down onto the body, thereby collapsing the mounting portion 121 towards the body. In this case, the air may escape the space 110 past the lip 123 and/or the one or more seals on the frame 3 of the pliable cover 1, in which case of the outlet 127 may be omitted. The thus created underpressure causes a leaching or desorption of the coupling agent 4 from the polymer layer 2 (in case of a polymer layer 2 encapsulating or otherwise containing the coupling agent 4), to replace the air evacuated from the space 110, in particular the air between the pliable cover 1 and the transducer elements 130 and the body of the subject 200, thereby improving the acoustic coupling between the ultrasound transducer elements 130 and the body. A small amount of a further coupling agent, e.g. a gel such as glycerine gel, may be applied between the pliable cover 1 and the body of the subject 200 to further promote this acoustic coupling. This for example is particularly beneficial in case the coupling agent 4 is only present between the pliable cover 1 and the individual ultrasound transducer elements 130.

Figure 9:
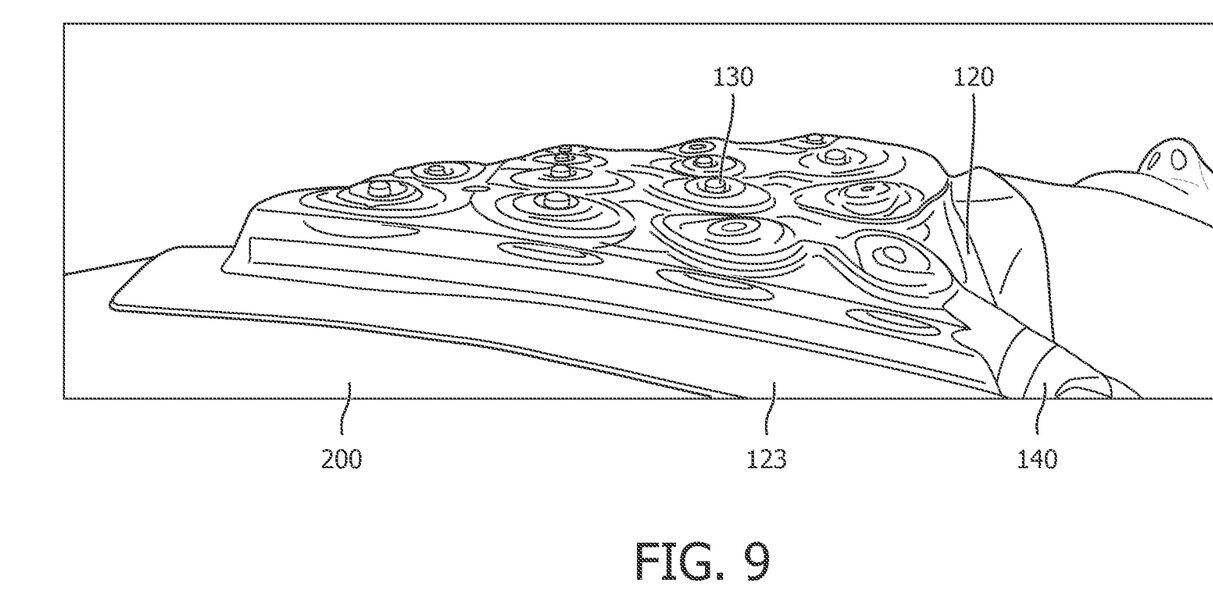
FIG. 9 is a photograph of the deployment of an ultrasound transducer probe assembly of FIG. 8 onto a patient's body.

The assembly may for example be applied to the body of a subject 200 as shown in the image in FIG. 9.

An ultrasound transducer probe may be applied to a body of a subject 200 in accordance with an embodiment of the following method. First, an ultrasound probe 100 including a probe body 120 having a mounting area 121 and optionally having a flexible lip 123 around said mounting area for sealing a space 110 between the mounting area and a subject 1 contacted by the ultrasound probe is provided. The probe may further comprise an outlet extending through the probe body for evacuating a volume of air from said space and further comprises an active area comprising a plurality of ultrasound transducer elements mounted in the mounting area Next, an embodiment of the pliable cover 1 is affixed over the active area to form an ultrasound probe assembly, which is subsequently positioned on a body region after which a volume of air is evacuated from the space 110 to create an underpressure in said space causing the pliable cover 1 to conform to the respective surfaces of the transducer elements 130. As explained above, this method may further comprise applying a gel to the body region prior to positioning the ultrasound probe assembly thereon.

Figure 10:
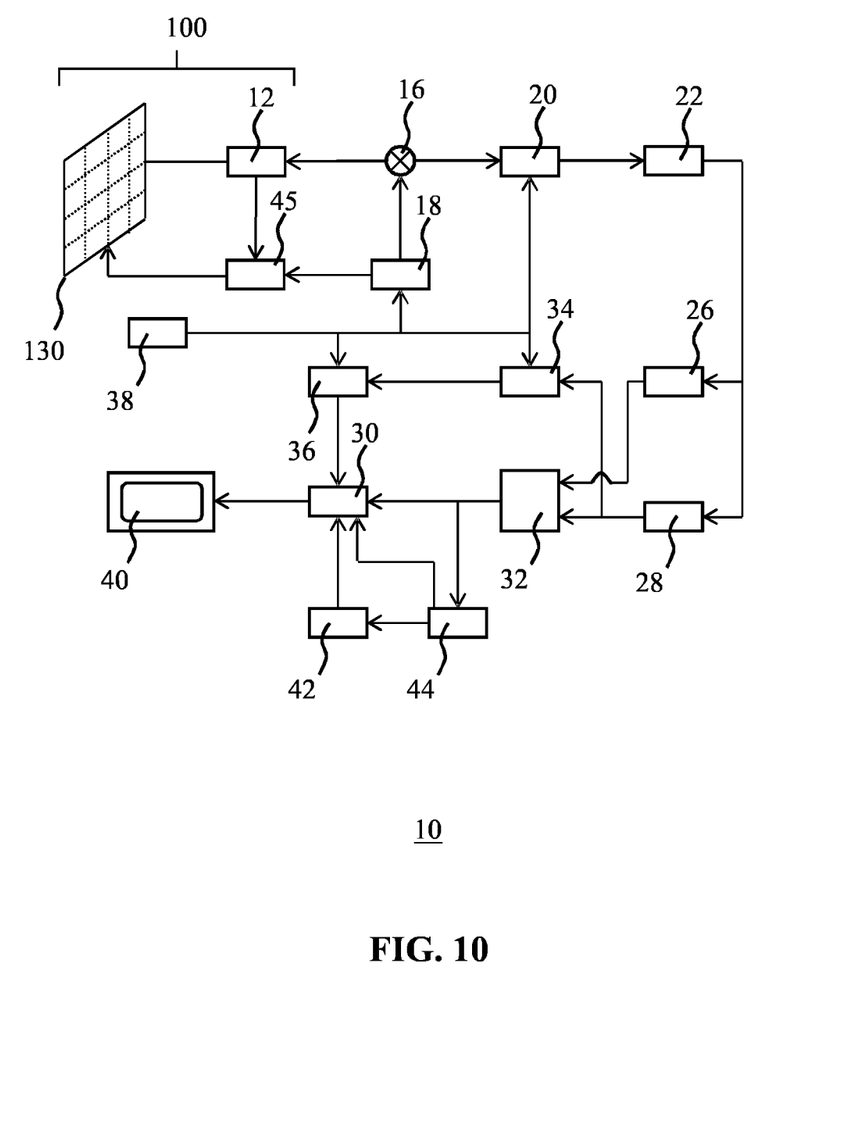
FIG. 10 schematically depicts a block diagram of an ultrasound system according to an example embodiment.

The ultrasound probe assembly according to embodiments of the present invention may form part of an ultrasound system 10. The ultrasound system 10 according to embodiments of the present invention may further comprise electronic circuitry for controlling the ultrasound probe 100 and for processing the ultrasound (pulse) echoes collected by the ultrasound probe 100 in case of an ultrasound diagnostic imaging system. Such electronic circuitry may at least partially be housed in a user console or the like as is well-known per se. FIG. 10 shows an example embodiment of the electronics that may be deployed to interface with and control the ultrasound probe 100 for the generation of ultrasound waves, e.g. ultrasound pulses, and reception of ultrasound echoes, e.g. pulse echoes, e.g. for diagnostic imaging purposes. The transducer array may be coupled to a microbeam former 12 in the probe 100 which controls transmission and reception of signals by the ultrasound transducer cells 100. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to a terminal, e.g. a user console device or the like, comprising a transmit/receive (T/R) switch 16 which switches between transmission and reception modes and protects the main beam former 20 from high energy transmit signals when a microbeam former is not present or used and the transducer array is operated directly by the main system beam former 20. The transmission of ultrasonic beams from the transducer array under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control the aforementioned voltage source 45 for the ultrasound transducer array 110. For instance, the voltage source 45 sets the DC and AC bias voltage(s) that are applied to CMUT elements of a CMUT array, e.g. to operate the CMUT elements in collapse mode, as is well-known per se. The transducer controller 18 may be further adapted to control the voltage supply 45 such as to switch the ultrasound transducer element tiles 130 to a low-power mode, e.g. in response to a temperature sensor signal indicative of the ultrasound transducer element tiles 130 reaching a critical temperature.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells 100. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system 10 is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 100 may not have 3D imaging capabilities and so on. Other variations will be apparent to the skilled person.

Moreover, it will be understood that the present invention is not limited to an ultrasonic diagnostic imaging system 10. The teachings of the present invention are equally applicable to ultrasonic therapeutic systems, e.g. HIFU ultrasound systems, in which the ultrasound transducer elements of the probe 100 may be operable in transmission mode only as there is no need to receive pulse echoes. As will be immediately apparent to the skilled person, in such therapeutic systems the system components described with the aid of FIG. 6 and required to receive, process and display pulse echoes may be omitted without departing from the teachings of the present application.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound probe assembly comprising:
   an ultrasound probe comprising: a probe body having a mounting area and a flexible lip around the mounting area, the flexible lip being configured to seal a space between the mounting area and a subject contacted by the ultrasound probe; and an active area comprising a plurality of ultrasound transducer elements mounted in the mounting area; and
   a pliable cover adapted to be applied over the active area of the ultrasound probe, the pliable cover comprising: a polymer layer adapted to hold a coupling agent that couples the ultrasound transducer elements to a body surface of the subject; and a regular pattern of channels extending through the pliable cover for evacuating air from between the pliable cover and the body surface, wherein: the channels are positioned such that when the pliable cover is applied over the active area, the channels are arranged in between the ultrasound transducer elements; and the mounting area is flexible and adapted to be deformed to conform to the body surface of the subject.

2. The ultrasound probe assembly of claim 1, wherein the pliable cover further comprises the coupling agent.

3. The ultrasound probe assembly of claim 1, wherein the coupling agent is contained by opposing polymers layers, wherein at least the polymer layer arranged to face the active area is porous or permeable to the coupling agent.

4. The ultrasound probe assembly of claim 1, wherein the coupling agent is dissolved or absorbed in the polymer layer.

5. The ultrasound probe assembly of claim 1, wherein the coupling agent is a liquid, an oil, an oil-based emulsion, a wax or a gel.

6. The ultrasound probe assembly of claim 1, wherein the pliable cover further comprises a frame affixed to an edge of the pliable cover, the frame being adapted to mount the pliable cover onto the ultrasound probe.

7. The ultrasound probe assembly of claim 1, wherein the pliable cover further comprises an adhesive edge region for adhering the pliable cover to the ultrasound probe.

8. The ultrasound probe assembly of claim 1, wherein the pliable cover has a thickness in a range of 10 μm to 1000 μm.

9. The ultrasound probe assembly of claim 1, wherein the pliable cover is affixed to the ultrasound probe.

10. An ultrasound system comprising the ultrasound probe assembly of claim 1.

11. A method of applying an ultrasound probe to a body region, the method comprising:
   providing an ultrasound probe including a probe body having a mounting area and a flexible lip around the mounting area for sealing a space between the mounting area and a subject contacted by the ultrasound probe, wherein the mounting area is flexible such that it may be deformed to conform to a body surface of the subject; and an active area comprising a plurality of ultrasound transducer elements mounted in the mounting area;
   affixing a pliable cover over the active area of the ultrasound probe to form an ultrasound probe assembly, the pliable cover comprising a polymer layer for containing a coupling agent for coupling the ultrasound transducer elements to the body surface of the subject and a regular pattern of channels extending through the pliable cover for evacuating air from between the pliable cover and the body surface, wherein the channels are positioned such that when the pliable cover is applied over the active area, the channels are arranged in between the ultrasound transducer elements;
   positioning the ultrasound probe assembly on the body region; and
   evacuating a volume of air from the space to create an underpressure in the space causing the pliable cover to conform to the respective surfaces of the transducer elements.

12. The method of claim 11, further comprising applying a gel to the body region prior to positioning the ultrasound probe assembly thereon.

13. An ultrasound probe assembly comprising:
an ultrasound probe, comprising: a probe body having a mounting area having a corrugated shape and a flexible lip around the mounting area, the flexible lip being configured to seal a space between the mounting area and a subject contacted by the ultrasound probe; an active area comprising a plurality of ultrasound transducer elements mounted in the mounting area; and a support member having pillars engaging with a pliable mounting area, each of the pillars being attached to a mounting portion for mounting an individual transducer element; and
a pliable cover adapted to be applied over the active area of the ultrasound probe, the pliable cover comprising: a polymer layer adapted to hold a coupling agent that couples the ultrasound transducer elements to a body surface of the subject; and a regular pattern of channels extending through the pliable cover for evacuating air from between the pliable cover and the body surface, wherein: the channels are positioned such that when the pliable cover is applied over the active area, the channels are arranged in between the ultrasound transducer elements: and the mounting area is flexible such that it may be deformed to conform to the body surface of the subject.

14. The ultrasound probe assembly of claim 13, wherein the pliable cover further comprises the coupling agent.

15. The ultrasound probe assembly of claim 13, wherein the coupling agent is contained by opposing polymers layers, and at least the polymer layer arranged to face the active area is porous or permeable to the coupling agent.

16. The ultrasound probe assembly of claim 13, wherein the coupling agent is dissolved or absorbed in the polymer layer.

17. The ultrasound probe assembly of claim 13, wherein the coupling agent is a liquid, an oil, an oil-based emulsion, a wax, or a gel.

18. The ultrasound probe assembly of claim 13, wherein the pliable cover further comprises a frame affixed to an edge of the pliable cover, the frame being adapted to mount the pliable cover onto the ultrasound probe.

19. The ultrasound probe assembly of claim 13, wherein the pliable cover further comprises an adhesive edge region for adhering the pliable cover to the ultrasound probe.

20. The ultrasound probe assembly of claim 13, wherein the pliable cover has a thickness in a range of 10 μm to 1,000 μm.

21. The ultrasound probe assembly of claim 13, wherein the pliable cover is affixed to the ultrasound probe.

* * * * *